US007028837B2

(12) United States Patent
Yanke et al.

(10) Patent No.: US 7,028,837 B2
(45) Date of Patent: Apr. 18, 2006

(54) RADIATION-SHIELDING SYRINGE CONTAINER

(75) Inventors: Paul Yanke, Oconomowoc, WI (US); Brian M. Schaber, West Allis, WI (US)

(73) Assignee: Vulcan Lead, Inc., Milwaukee, WI (US)

( * ) Notice: Subject to any disclaimer, the term of this patent is extended or adjusted under 35 U.S.C. 154(b) by 0 days.

(21) Appl. No.: 10/301,961

(22) Filed: Nov. 22, 2002

(65) Prior Publication Data

US 2003/0141210 A1 Jul. 31, 2003

Related U.S. Application Data

(60) Provisional application No. 60/332,610, filed on Nov. 23, 2001.

(51) Int. Cl.
*G21F 5/018* (2006.01)
*A61N 5/00* (2006.01)

(52) U.S. Cl. ................ 206/364; 250/506.1; 250/515.1; 600/5

(58) Field of Classification Search ........ 206/363–365, 206/524.4; 250/506.1, 507.1, 515.1; 600/5
See application file for complete search history.

(56) References Cited

U.S. PATENT DOCUMENTS

| | | | | |
|---|---|---|---|---|
| 4,825,088 | A * | 4/1989 | Nair et al. | 250/506.1 |
| 5,519,931 | A * | 5/1996 | Reich | 29/426.3 |
| 5,536,945 | A * | 7/1996 | Reich | 250/507.1 |
| 5,560,511 | A * | 10/1996 | McNerney | 220/327 |
| 5,611,429 | A * | 3/1997 | Phillips | 206/365 |
| 5,672,883 | A * | 9/1997 | Reich | 250/507.1 |
| 5,918,443 | A * | 7/1999 | Phillips | 206/365 |
| RE36,693 | E * | 5/2000 | Reich | 250/507.1 |
| 6,155,420 | A * | 12/2000 | Phillips | 206/364 |
| 6,166,391 | A * | 12/2000 | Strine et al. | 250/507.1 |
| 6,425,174 | B1 * | 7/2002 | Reich | 29/469 |
| 6,576,918 | B1 * | 6/2003 | Fu et al. | 250/507.1 |
| 6,722,499 | B1 * | 4/2004 | Reich | 206/365 |

* cited by examiner

*Primary Examiner*—Bryon P. Gehman
(74) *Attorney, Agent, or Firm*—Michael Best & Friedrich LLP

(57) ABSTRACT

A radiation-shielding container assembly defines a central axis and includes an elongated body portion having a closed end, an open end, and an outer surface extending between the open and closed ends. An inner surface is spaced radially inwardly from the outer surface, and a frusto-conical body surface extends radially inwardly from the outer surface adjacent the open end. A cap portion of the container is securable to the body portion and includes a closed end and an open end that is spaced from the closed end. The open end includes a frusto-conical cap surface that is matingly engageable with the frusto-conical body surface such that when the cap portion is secured to the body portion, the frusto-conical body surface and the frusto-conical cap surface overlap each other along a plane that is perpendicular to the axis, thereby preventing a straight-line path for radiation to escape from the container.

21 Claims, 5 Drawing Sheets

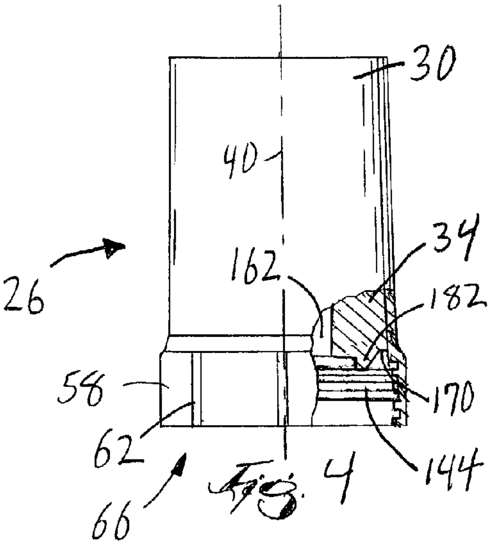
Fig. 4
Fig. 10
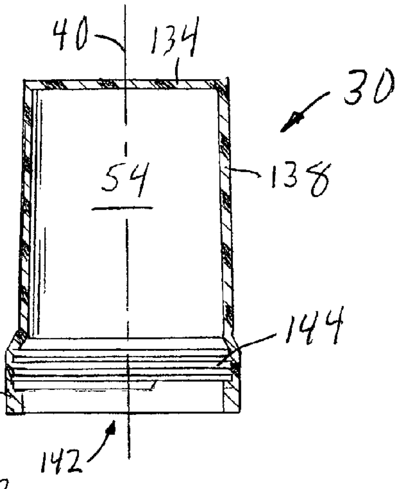
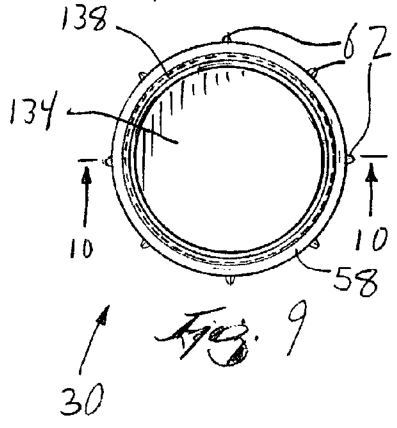
Fig. 9
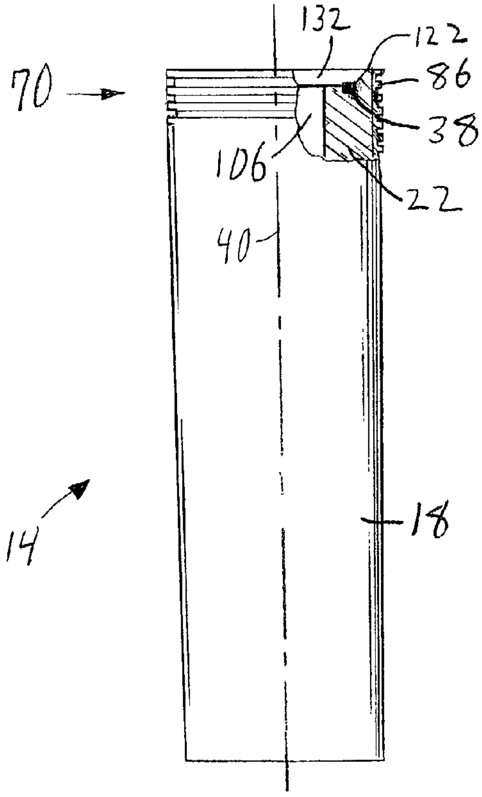
Fig. 3
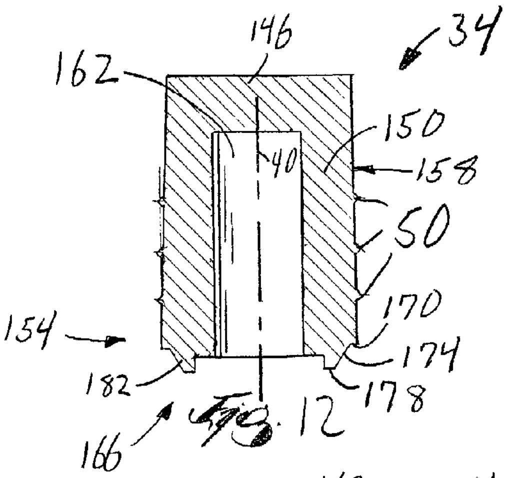
Fig. 12
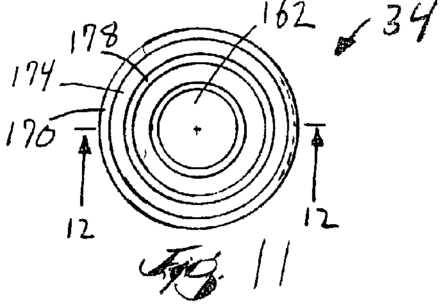
Fig. 11

RADIATION-SHIELDING SYRINGE CONTAINER

This application claims the benefit of provisional application No. 60/332,610 filed Nov. 23, 2001.

FIELD OF THE INVENTION

The invention relates to shielded containers, and more particularly to shielded containers configured to hold a radiopharmaceutical.

BACKGROUND OF THE INVENTION

Radiation-shielding containers for storing, transporting, and dispensing radioactive drugs are known in the art. Radioactive drugs, commonly known as radiopharmaceuticals, are used to treat a variety of illnesses. However, technicians and medical personnel who handle these drugs on a regular basis must take precautions to reduce their exposure to the radiation emitted by radiopharmaceuticals. These precautions include, among other things, the use of radiation-shielding containers to store radiopharmaceuticals.

Accordingly, radiation-shielding containers that are configured to hold vials of radiopharmaceutical liquid are known. Some containers provide access ports or other openings such that a liquid contained therein can be withdrawn from the vials using a syringe. Other containers exist that are configured to hold an individual syringe that contains radiopharmaceutical liquid. The syringe container is popular among hospitals and other care facilities because the radiopharmaceutical can be shipped and stored in premeasured doses, thereby reducing the equipment and labor costs associated with storing and handling large quantities of radiopharmaceuticals.

SUMMARY OF THE INVENTION

In one embodiment, the invention provides a radiation-shielding container assembly. The assembly includes an elongated body portion that has a closed end, an open end, an outer surface defining a central axis, and an inner surface spaced radially inwardly from the outer surface. An outer body interface extends radially inwardly from the outer surface, and a transition surface extends from the outer body interface toward the inner surface. The transition surface defines a frusto-conical body surface that surrounds the central axis. The assembly also includes a cap portion that is securable to the body portion. The cap portion includes a closed end and an open end that is spaced from the closed end. The open end includes a frusto-conical cap surface that surrounds the open end and is matingly engageable with the transition surface. As such, when the cap portion is secured to the body portion, the frusto-conical cap surface and the frusto-conical body surface overlap along a plane lying perpendicular to the central axis.

In another embodiment, the invention also provides a radiation-shielding container that is configured to receive a syringe having opposed ends and containing a radiopharmaceutical. The container includes a first radiation shield that is configured to receive a first end of the syringe, and a first casing that at least partially surrounds the first radiation shield. The container also includes a second radiation shield that is configured to receive a second end of the syringe, and a second casing that at least partially surrounds the second radiation shield and is securable to the first casing. The container is configured such that when the second casing is secured to the first casing, the first and second radiation shields overlap to preclude a straight-line path for radiation emitted by the radiopharmaceutical to pass from the container.

In another embodiment, the invention further provides a radiation-shielding container for a syringe that contains a radioactive liquid. The syringe container includes a generally cylindrical body casing that has a central axis and a cap-engaging portion. The container also includes a first radiation-shielding liner that is received within the body casing. The first liner defines a first chamber that has a first chamber opening that is surrounded by a first interface surface. The container further includes a generally cylindrical cap casing having a body-engaging portion that is engagable with the cap-engaging portion to releasably secure the cap to the body. A second radiation-shielding liner is received within the cap casing and defines a second chamber that has a second chamber opening surrounded by a second interface surface. An interface plane extends across one of the chamber openings and is substantially perpendicular to the central axis. As such, when the cap is secured to the body, each interface surface includes portions lying on each side of the interface plane.

Other features of the invention will become apparent to those skilled in the art upon review of the following detailed description and drawings.

BRIEF DESCRIPTION OF THE DRAWINGS

FIG. 3 is a side view, with a portion cut away, of the body portion of the radiation-shielding container of FIG. 1.

FIG. 4 is a side view, with a portion cut away, of the cap portion of the radiation-shielding container of FIG. 1.

FIG. 9 is an end view of the outer cap portion of the radiation-shielding container of FIG. 1.

FIG. 10 is a section view taken along line 10—10 of FIG. 9.

FIG. 11 is an end view of the inner cap portion of the radiation-shielding container of FIG. 1.

FIG. 12 is a section view taken along line 12—12 of FIG. 11.

Figure 1:
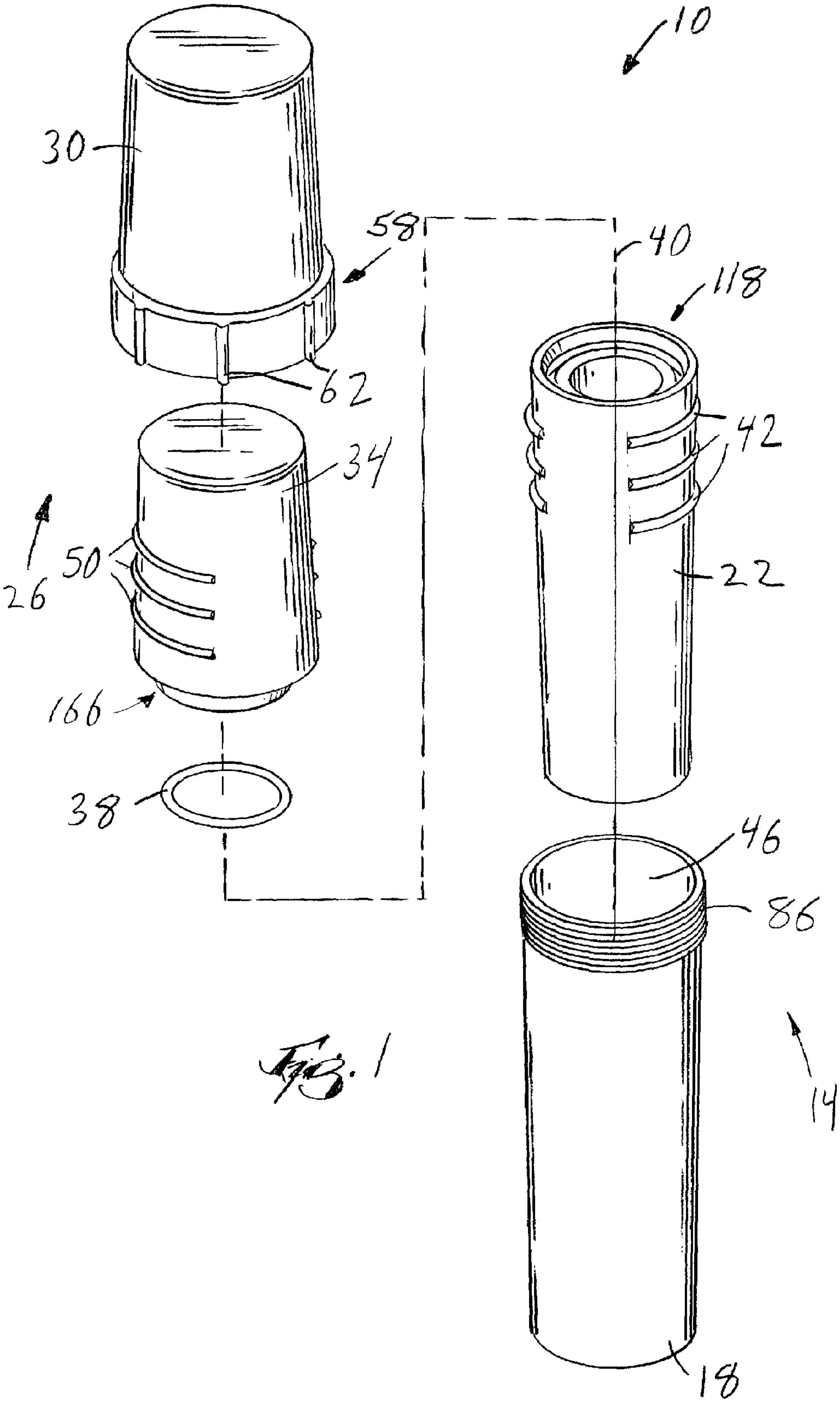
FIG. 1 is an exploded perspective view of a radiation-shielding container of the present invention.

Before one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items.

DETAILED DESCRIPTION OF THE PREFERRED EMBODIMENT

The drawings illustrate a radiation-shielding syringe container 10 embodying the invention. With reference to FIG. 1, the container 10 includes a body 14 including an outer protective portion or body casing 18 and an inner radiation-shielding body liner 22 that is received within the outer body portion 18. The container 10 also includes a cap 26 that is securable to the body 14 and includes an outer protective portion or cap casing 30 and an inner radiation-shielding cap liner 34 that is received within the outer cap portion 30. The container 10 also includes a resilient O-ring 38 that provides a liquid-tight seal between the body 14 and the cap 26 when the two are secured to one another. A central axis 40 of the container 10 extends through the cap 26 and the body 14.

The body liner 22 includes a plurality of circumferentially extending ribs 42 that grip an inner surface 46 of the outer portion 18 and substantially secure the body liner 22 to the outer portion 18 upon initial assembly of the portions 18, 22. Similarly, the cap liner 34 includes a plurality of circumferentially extending ribs 50 that grip an inner surface 54 (see FIG. 2) of the outer portion 30. Adhesives and the like can also be used to secure the outer portions 18, 30 to the liners 22, 34.

Figure 2:
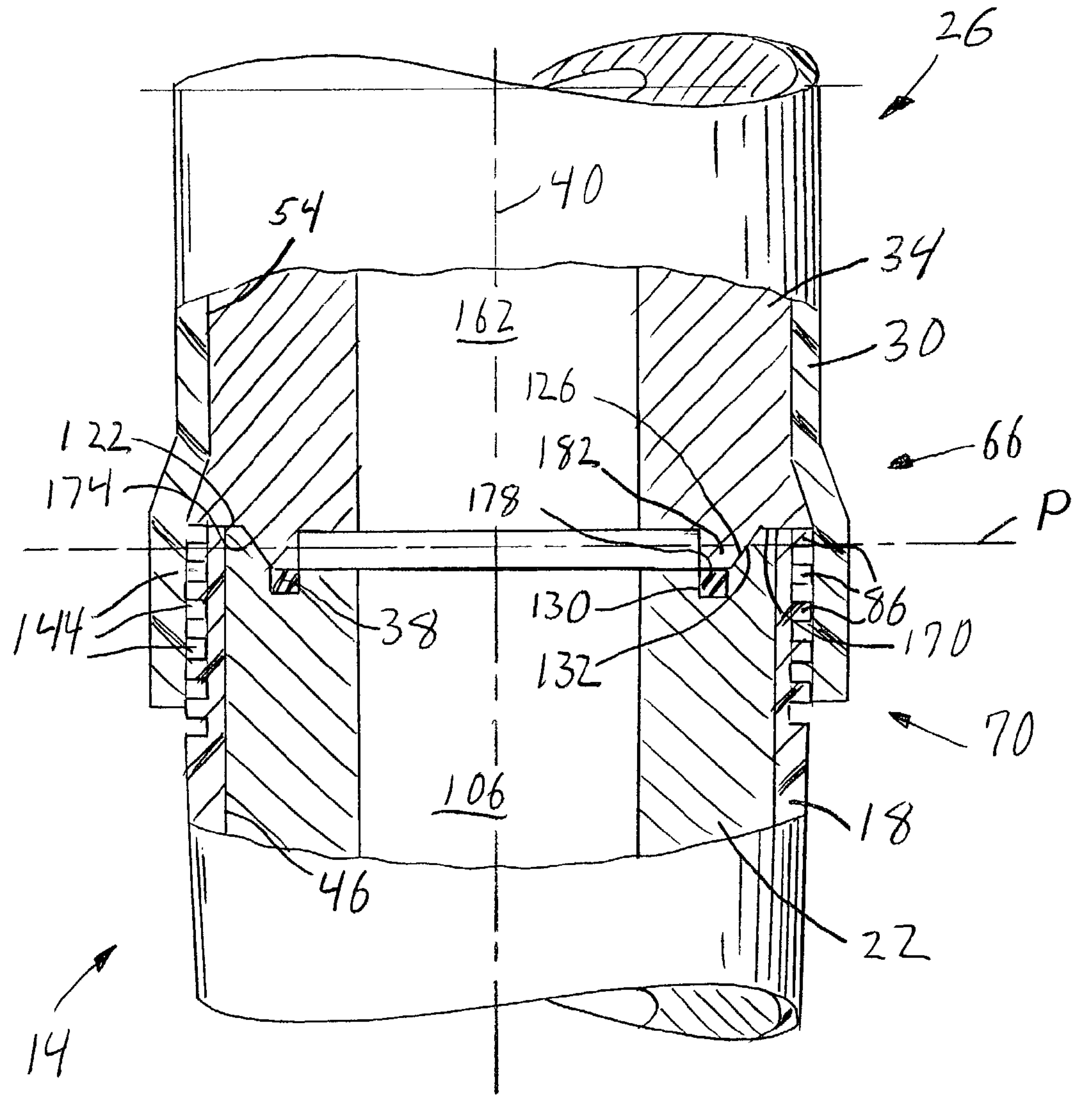
FIG. 2 is an enlarged view, partially in section, of the radiation-shielding container of FIG. 1.

Referring now also to FIGS. 2–4, the outer cap portion 30 includes a grip portion 58 (see FIG. 4) having a plurality of radially protruding and axially extending ribs 62. The ribs 62 provide additional gripping surfaces for use when the cap 26 is secured to and removed from the body 14. The ribs 62 also substantially prevent unwanted rolling of the container 10 when the container 10 is in a non-upright position. The cap 26 includes a body-engaging portion 66 and the body 14 includes a cap-engaging portion 70. The engaging portions 66, 70 are configured to engage each other to secure the cap 26 to the body 14. Preferably, the cap 26 and body 14 are threadedly engaged to each other as shown and described below, however other types of engagement can also be used.

Figure 5:
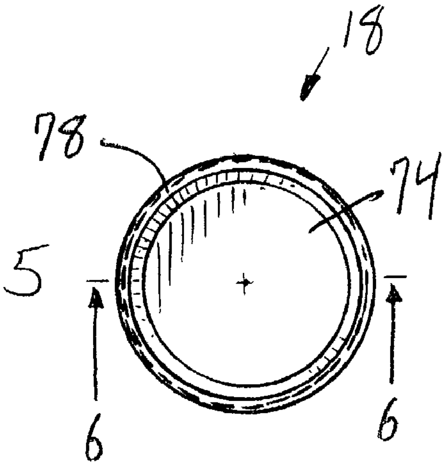
FIG. 5 is an end view of the outer body portion of the radiation-shielding container of FIG. 1.
Figure 6:
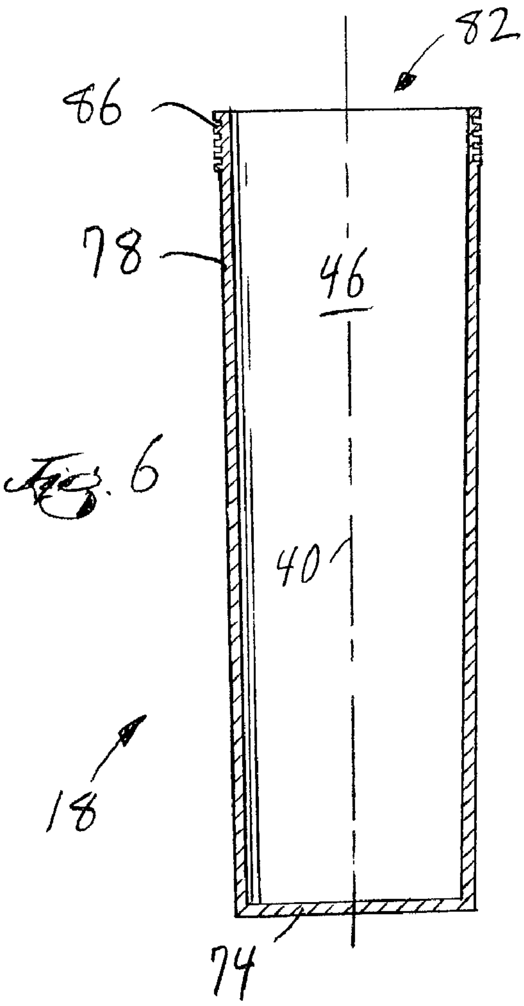
FIG. 6 is a section view taken along line 6—6 of FIG. 5.

Referring now to FIGS. 5 and 6, the outer body portion 18 is preferably made of a polymeric material that protects the body liner 22 from dents, dings, scratches, and the like. The outer body portion 18 includes a generally circular end wall 74 and an outer wall 78 extending axially from the end wall 74 to define an open end 82 of the outer body portion 18. External threads 86 are formed on the outer wall 78 and surround the open end 82.

Figure 7:
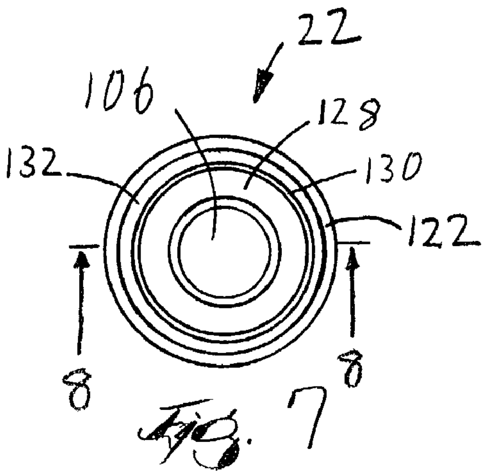
FIG. 7 is an end view of the inner body portion of the radiation-shielding container of FIG. 1.
Figure 8:
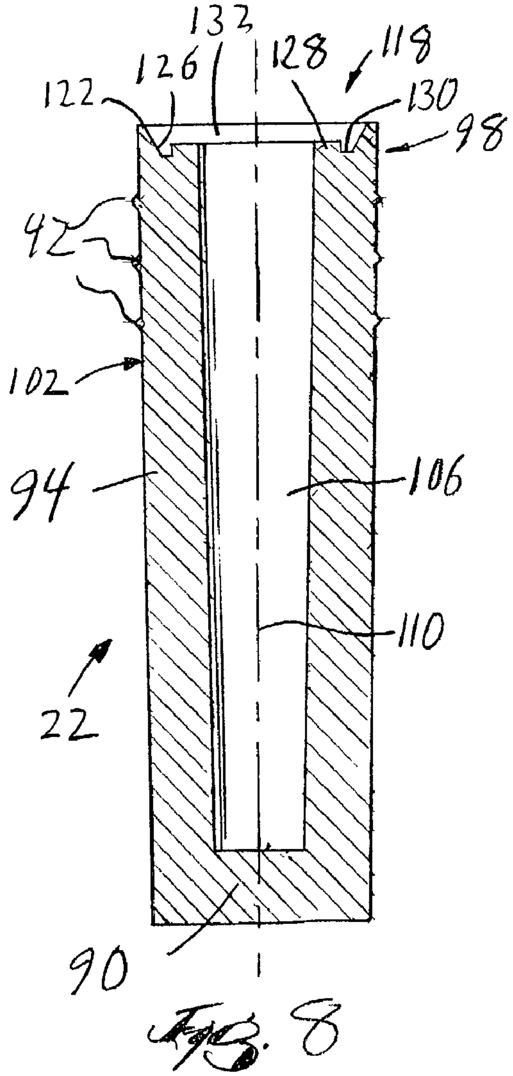
FIG. 8 is a section view taken along line 8—8 of FIG. 7.

Referring now to FIGS. 7 and 8, the body liner 22 is preferably made at least partially of radiation-shielding materials such as lead and/or tungsten. As used herein, "radiation-shielding" generally refers to the efficient absorption of incident high-energy radiation such as X-ray, gamma and beta radiation so that appreciable attenuation occurs within a relatively short path. Other materials that are suitable for radiation-shielding applications include, among other things, bismuth, depleted uranium, tin, copper, silver, nickel stainless steel, and various alloys and mixtures thereof. The body liner 22 includes a substantially circular end wall 90 and an outer wall 94 that extends from the end wall 90 toward an open end 98 of the body liner 22. The ribs 42 discussed above are formed on an outer surface 102 of the outer wall 94. The outer wall 94 substantially defines a syringe-receiving chamber 106 and a central axis 110. The chamber 106 is sized and configured to receive the body portion of a syringe (not shown). The open end 98 of the body liner 22 provides a first interface 118. The first interface 118 includes an outer cap liner interface 122, a transition surface 126, and an inner interface 128. An annular groove 130 is formed in the inner interface 128 and receives the O-ring 38. The transition surface 126 extends radially and axially inwardly toward the chamber 106 and defines a frusto-conical recess 132 that engages the cap liner 34 as described below.

Referring now to FIGS. 9 and 10, the outer cap portion 30 is preferably made of a polymeric material that protects the cap liner 34 from dents, dings, scratches, and the like. The outer cap portion 30 includes a generally circular end wall 134 and an outer wall 138 extending axially from the end wall 134 to define an open end 142 of the outer cap portion 30. Internal threads 144 are formed in the grip portion 58 and surround the open end 142.

Referring now to FIGS. 11 and 12, the cap liner 34 is preferably made at least partially of the above described radiation-shielding materials. The cap liner 34 includes a substantially circular end wall 146 and an outer wall 150 that extends axially from the end wall 146 to define an open end 154 of the cap liner 34. The ribs 50 discussed above are formed on an outer surface 158 of the outer wall 150. The outer wall 150 substantially defines a syringe-receiving chamber 162 sized and configured to receive the plunger portion of a syringe (not shown). The syringe-receiving chambers 106, 162 cooperate to completely enclose the syringe when the cap 26 is secured to the body 14. The open end 154 of the cap liner 34 provides a second interface 166. The second interface 166 includes an outer body liner interface 170, a transition surface 174, and an inner interface 178. The transition surface 174 extends radially inwardly and axially away from the outer body liner interface 170 and defines a frusto-conical protrusion 182 that is received in the frusto-conical recess 132 of the body liner 22. The inner interface 178 is a substantially annular surface configured to cover the annular groove 130 in the body liner 22 such that the O-ring 38 is compressed between the groove 130 and the inner interface 178 when the cap 26 is secured to the body 14.

Referring to FIG. 2, the cap 26 is assembled with the body 14 by threadedly engaging the internal threads 144 with the external threads 86. As the cap 26 is drawn toward the body 14, the frusto-conical protrusion 182 is received in the frusto-conical recess 132 such that the two overlap each other along an interface plane P lying perpendicular to the central axis. When the cap 26 is fully tightened onto the body 14, the O-ring 38 is deformed between the annular groove 130 and the inner interface 178, the transition surfaces 126, 174 matingly engage each other, and the outer cap liner interface 122 matingly engages the outer body liner interface 170. As such, radiation emitted from a radiopharmaceutical contained in the chambers 106, 162 is substantially absorbed by the walls 90, 94, 146, 150 of the shielding portions 22, 34, and by the overlapping frusto-conical recess 132 and protrusion 182. Specifically, the overlapping arrangement of the frusto-conical protrusion 182 and the frusto-conical recess 132 prevents a straight-line path for radiation emitted from inside the chambers 106, 162 to pass from the chambers 106, 162 to the outer surroundings of the container 10. The O-ring 38 offers additional radiation protection by substantially sealing the container 10 such that radioactive fluid can not leak past the overlapping portions (e.g. the protrusion 182 and the recess 132) should the radioactive fluid leak or otherwise spill from the syringe.

It should be appreciated that the particular configuration of the cap 14 and body 26 are not limited with respect to the configuration of the threaded portions 86, 144, and the frusto-conical portions 132, 182. For example, the outer cap portion 30 can include external threads formed around the open end 142 and the outer body portion 18 can include internal threads formed around the open end 118. Similarly, the cap liner 34 can include a frusto-conical recess whereas the body liner 22 would then include a frusto-conical protrusion.

Figure 13:
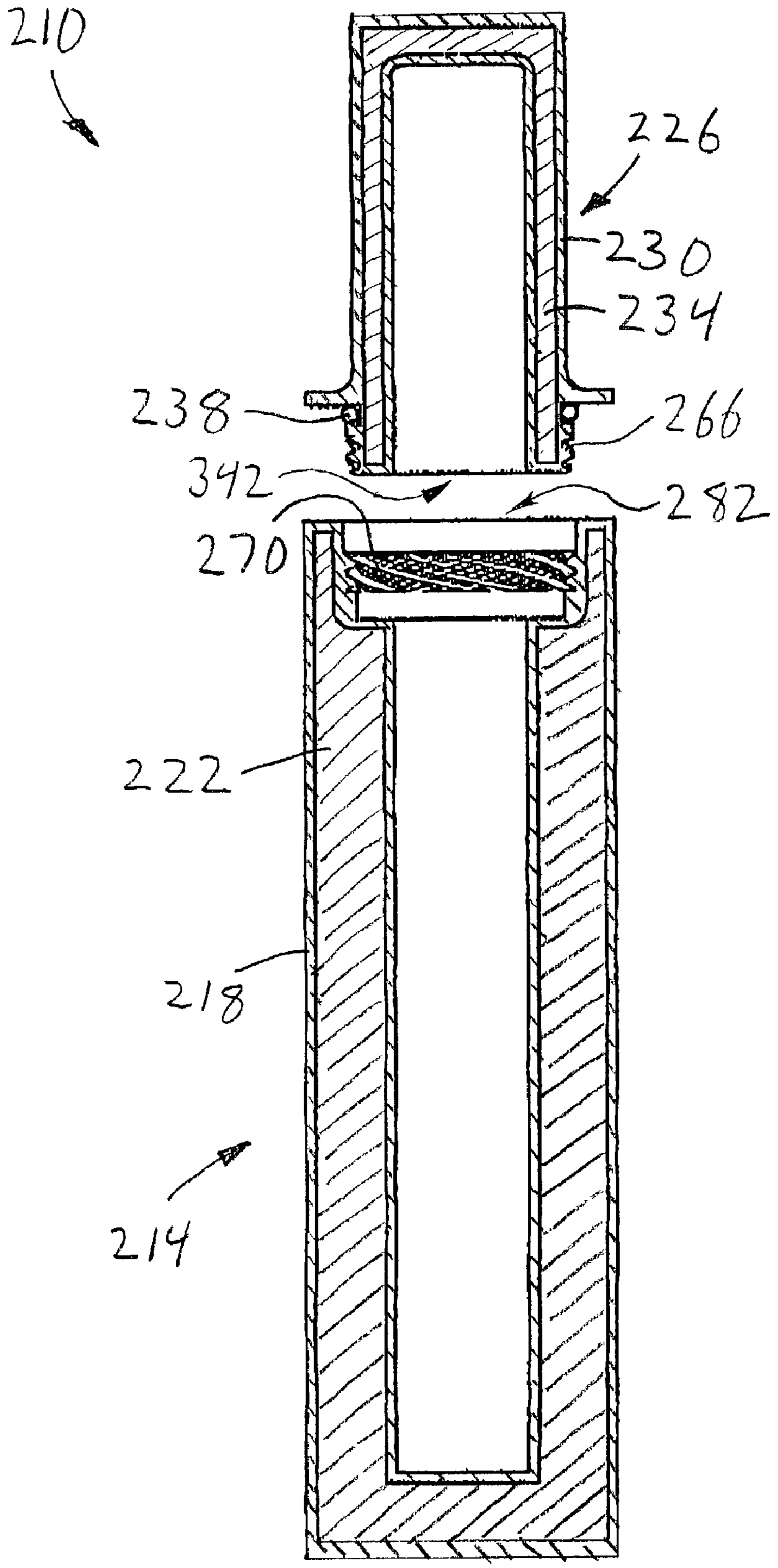
FIG. 13 is a section view of a radiation-shielding container that is an alternative embodiment of the invention.

FIG. 13 illustrates a radiation shielding container 210 that is an alternative embodiment of the invention. Features and components of the container 210 that are the same or similar to the features and components of the container 10 have been given like reference numerals, increased by two hundred. The container 210 includes a body 214 including an outer protective portion 218 and an inner radiation-shielding body liner 222. The container 210 also includes a cap 226 that is securable to the body 214 and includes an outer protective portion 230 and an inner radiation-shielding cap liner 234. A resilient O-ring 238 is positioned on the cap 226 and provides a liquid-tight seal between the body 214 and the cap 226 when the two are secured to one another.

The outer body portion 218 and the outer cap portion 230 of the container 210 substantially completely surround the body liner 222 and the cap liner 234. In some embodiments, the outer portions 218, 230 are formed by overmolding the outer portions 218, 230, which can be polymeric, around the liners 222, 234. The liners 222, 234 can be formed from substantially any of the radiation-shielding materials discussed above.

The cap 226 includes a body-engaging portion 266 in the form of external threads, and the body 214 includes a cap-engaging portion 270 in the form of internal threads. The illustrated threads are formed in the outer portions 218, 230 and are provided with a plurality of thread leads, each thread lead having a relatively large thread pitch. In this regard, a relatively small amount of relative rotation between the cap 226 and the body 214 (e.g. one-quarter of a turn) is required to open and close the container 210, while maintaining an adequate structural coupling between the cap 226 and the body 214 when the two are connected.

The body 214 includes an open end 282 that is sized to receive an open end 342 of the cap 226. When the cap 226 and the body 214 are secured together, portions of the cap liner 234 and the body liner 222 overlap each other in the axial direction. The overlapping nature of the cap liner 234 and the body liner 222 when the container 210 is closed is sufficient to substantially prevent a straight-line path for radiation emitted from inside the container 210 to pass from the container 210 to the outer surroundings. It should be noted that the cap liner 234 and the body liner 222 of the container 210 do not intimately engage one another, however adequate absorption of emitted radiation is maintained. The overmolded configuration of the outer portions 218, 230 protects the liners 222, 234 from dents, dings, scratches and the like.

Various features of the invention are set forth in the following claims.

What is claimed is:

1. A radiation-shielding container assembly comprising:

an elongated body portion including an inner liner and an outer sheath surrounding the liner, the body portion further having a closed end, a free open end, an outer surface extending between the free open and closed ends and defining a central axis, an inner surface spaced radially inwardly from the outer surface, the inner liner including an outer body interface extending radially inwardly from the outer surface adjacent the open end, and a transition surface extending from the outer body interface toward the inner surface and defining a frusto-conical body surface surrounding the axis at the free open end of the body portion, and a cap portion securable to the body portion, the cap portion including an inner liner and an outer sheath surrounding the liner, the cap portion further including a closed end and a free open end spaced from the closed end, the inner liner of the cap portion at the free open end defining a frusto-conical cap surface surrounding the free open end and matingly engageable with the transition surface such that when the cap portion is secured to the body portion, the frusto-conical cap surface and the frusto-conical body surface overlap along a plane that is substantially perpendicular to the central axis.

2. The radiation-shielding container assembly of claim 1 wherein the transition surface includes an inner cap interface surrounding the axis and extending toward the inner surface along a plane extending substantially normal to the axis.

3. The radiation-shielding container assembly of claim 1, wherein the inner liner of the body portion is a radiation-shielding liner, and the outer sheath of the body portion is a protective sheath.

4. The radiation-shielding container assembly of claim 3, wherein the radiation-shielding liner is made of lead and the outer protective sheath is made of a polymer.

5. The radiation-shielding container assembly of claim 1, wherein the inner liner of the cap portion is a radiation-shielding liner, and the outer sheath of the cap portion is a protective sheath.

6. The radiation-shielding container assembly of claim 5, wherein the radiation-shielding liner is made of lead and the outer protective sheath is made of a polymer.

7. The radiation-shielding container assembly of claim 1, wherein the body portion includes a threaded portion surrounding the open end and the cap portion includes a threaded portion surrounding the open end, the threaded portions configured for threaded engagement with each other to secure the cap portion and the body portion to each other.

8. The radiation-shielding container assembly of claim 1, wherein the body portion includes an annular groove surrounded by the frusto-conical body surface, the container assembly further comprising a resilient O-ring positioned in the annular groove.

9. The radiation-shielding container assembly of claim 1, wherein the cap portion includes a plurality of radially projecting and axially extending ridges surrounding the open end.

10. A radiation-shielding container configured to receive a syringe having opposite first and second ends and that contains a radiopharmaceutical, the container comprising:

a first radiation shield configured to receive the first end of the syringe, the first radiation shield including an outer surface, an inner surface and an interface surface extending between the outer surface and the inner surface at a free open end of the first radiation shield;

a first casing at least partially surrounding the first radiation shield and having a longitudinal axis;

a second radiation shield configured to receive the second end of the syringe, the second radiation shield including an outer surface, an inner surface and an interface surface extending between the outer surface and the inner surface at a free open end of the second radiation shield;

a second casing at least partially surrounding the second radiation shield and securable to the first casing;

wherein when the second casing is secured to the first casing, portions of each of the interface surfaces engage one another and overlap along a plane that is substantially perpendicular to the longitudinal axis to preclude a straight-line path for radiation emitted by the radiopharmaceutical to pass from the container.

11. The radiation-shielding container of claim 10, wherein the first casing and the second casing are made of plastic.

12. The radiation-shielding container of claim 10, wherein the first radiation shield and the second radiation shield are made of lead.

13. The radiation-shielding container of claim 10, wherein the interface surface of the first shield defines a frusto-conical recess and the interface surface of the second shield defines a frusto-conical protrusion that is received in the frusto-conical recess when the second casing is secured to the first casing, thereby precluding a straight-line path for radiation emitted by the radiopharmaceutical to pass from the container.

14. The radiation-shielding container of claim 10, further comprising a resilient O-ring secured between the first shield and the second shield.

15. The radiation-shielding container of claim 10, wherein the first casing includes an externally threaded portion and the second casing includes an internally threaded portion configured for threaded engagement with the externally threaded portion to secure the second casing to the first casing.

16. The radiation-shielding container of claim 10, wherein the second casing includes a plurality of ridges surrounding one end.

17. A radiation-shielding container for a syringe that contains a radio-active liquid, the syringe container comprising:

a generally cylindrical body casing having a central axis, the body casing also including a cap-engaging portion having a threaded portion;

a first radiation-shielding liner received within the body casing, the first liner defining a first chamber having a first chamber opening surrounded by a first interface surface;

a generally cylindrical cap casing including a body-engaging portion having a threaded portion wherein the threaded portion of the body-engaging portion is engagable with the threaded portion of the cap-engaging portion to releasably secure the cap to the body;

a second radiation-shielding liner received within the cap casing, the second liner defining a second chamber having a second chamber opening surrounded by a second interface surface; and an interface plane extending across one of the chamber openings and being substantially perpendicular to the central axis, wherein when the cap is secured to the body, each of the interface surfaces includes portions lying on each side of the interface plane and the interface surfaces engage one another.

18. The radiation-shielding container of claim 17, wherein the body casing and the cap casing are each made of plastic.

19. The radiation-shielding container of claim 17, wherein the first and second radiation-shielding liners are each made of lead.

20. The radiation-shielding container of claim 17, wherein the cap casing includes a plurality of radially projecting and axially extending ridges surrounding the body-engaging portion.

21. The radiation-shielding container of claim 17, wherein the first and second interface surfaces are generally frusto-conical.

* * * * *